United States Patent
Chitre et al.

(10) Patent No.: US 10,213,229 B2
(45) Date of Patent: Feb. 26, 2019

(54) LEAD INSERTION DEVICES AND ASSOCIATED SYSTEMS AND METHODS

(71) Applicant: Nevro Corporation, Redwood City, CA (US)

(72) Inventors: Yougandh Chitre, Santa Clara, CA (US); Andre B. Walker, Monte Sereno, CA (US); Vivek Sharma, San Ramon, CA (US)

(73) Assignee: Nevro Corp., Redwood City, CA (US)

( * ) Notice: Subject to any disclaimer, the term of this patent is extended or adjusted under 35 U.S.C. 154(b) by 279 days.

(21) Appl. No.: 15/085,913

(22) Filed: Mar. 30, 2016

(65) Prior Publication Data

US 2016/0302827 A1   Oct. 20, 2016

Related U.S. Application Data

(62) Division of application No. 13/710,341, filed on Dec. 10, 2012, now Pat. No. 9,308,022.

(51) Int. Cl.
*A61B 17/34* (2006.01)
*A61N 1/05* (2006.01)

(52) U.S. Cl.
CPC ...... *A61B 17/3468* (2013.01); *A61B 17/3401* (2013.01); *A61B 17/3417* (2013.01); *A61N 1/0551* (2013.01)

(58) Field of Classification Search
CPC ............ A61B 17/3417; A61B 17/3468; A61B 17/3401; A61B 17/3415; A61B 19/00; A61B 17/34
See application file for complete search history.

(56) References Cited

U.S. PATENT DOCUMENTS

| 3,774,618 A | 11/1973 | Avery |
| 4,136,703 A | 1/1979 | Wittkampf |
| 4,141,365 A | 2/1979 | Fischell et al. |
| 4,285,347 A | 8/1981 | Hess |
| 4,374,527 A | 2/1983 | Iversen |

(Continued)

FOREIGN PATENT DOCUMENTS

| CN | 101920065 A | 12/2010 |
| EP | 0158316 A2 | 10/1985 |

(Continued)

OTHER PUBLICATIONS

Calthorpe et al., "The History of Spinal Needles: getting to the point," Anaesthesia, vol. 59, 2004, 11 pages.

(Continued)

*Primary Examiner* — Victor Nguyen
(74) *Attorney, Agent, or Firm* — Perkins Coie LLP

(57) ABSTRACT

Insertion devices and associated systems and methods for the percutaneous placement of patient leads are disclosed herein. A system in accordance with a particular embodiment includes a cannula having a lumen and a first dilator. The first dilator can be positioned within the lumen and the first dilator and the cannula can be used to create a percutaneous entry point. An additional dilator can be positioned over the first dilator and advanced into the percutaneous entry point to expand the percutaneous entry point. A final dilator can be inserted into the patient and two leads can be advanced into the patient through the final dilator.

10 Claims, 13 Drawing Sheets

(56) References Cited

U.S. PATENT DOCUMENTS

| | | | |
|---|---|---|---|
| 4,379,462 A | 4/1983 | Borkan et al. | |
| 4,383,532 A | 5/1983 | Dickhudt | |
| 4,414,986 A | 11/1983 | Dickhudt et al. | |
| 4,465,079 A | 8/1984 | Dickhudt | |
| 4,466,690 A | 8/1984 | Osypka | |
| 4,498,482 A | 2/1985 | Williams | |
| 4,573,448 A * | 3/1986 | Kambin | A61B 17/3417 128/898 |
| 4,683,895 A | 8/1987 | Pohndorf | |
| 4,764,132 A | 8/1988 | Stutz, Jr. | |
| 4,796,642 A | 1/1989 | Harris | |
| 4,898,173 A | 2/1990 | Daglow et al. | |
| 4,919,653 A | 4/1990 | Martinez et al. | |
| 4,934,367 A | 6/1990 | Daglow et al. | |
| 5,070,605 A | 12/1991 | Daglow et al. | |
| 5,072,458 A | 12/1991 | Suzuki | |
| 5,081,990 A | 1/1992 | Deletis | |
| 5,106,376 A | 4/1992 | Mononen et al. | |
| 5,121,754 A | 6/1992 | Mullett | |
| 5,129,404 A | 7/1992 | Spehr et al. | |
| 5,179,962 A | 1/1993 | Dutcher et al. | |
| 5,190,529 A | 3/1993 | McCrory et al. | |
| 5,257,636 A | 11/1993 | White | |
| 5,354,326 A | 10/1994 | Comben et al. | |
| 5,360,441 A | 11/1994 | Otten | |
| 5,392,791 A | 2/1995 | Nyman et al. | |
| 5,458,629 A | 10/1995 | Baudino et al. | |
| 5,480,421 A | 1/1996 | Otten | |
| 5,562,722 A | 10/1996 | Racz et al. | |
| 5,669,882 A | 9/1997 | Pyles | |
| 5,690,117 A | 11/1997 | Gilbert | |
| 5,730,628 A | 3/1998 | Hawkins | |
| 5,843,148 A | 12/1998 | Gijsbers | |
| 5,846,226 A | 12/1998 | Urmey | |
| 5,871,531 A | 2/1999 | Struble | |
| 5,895,416 A | 4/1999 | Barreras | |
| 5,902,236 A | 5/1999 | Iversen | |
| 5,935,159 A | 8/1999 | Cross, Jr. et al. | |
| 5,957,912 A | 9/1999 | Heitzmann | |
| 5,983,126 A | 11/1999 | Wittkampf | |
| 6,024,702 A | 2/2000 | Iversen | |
| 6,055,456 A | 4/2000 | Theodore | |
| 6,104,960 A | 8/2000 | Duysens | |
| 6,106,460 A | 8/2000 | Panescu et al. | |
| 6,154,678 A | 11/2000 | Lauro | |
| 6,161,047 A | 12/2000 | King et al. | |
| 6,185,463 B1 | 2/2001 | Baudino | |
| 6,192,278 B1 | 2/2001 | Werner et al. | |
| 6,205,361 B1 | 3/2001 | Kuzma et al. | |
| 6,214,016 B1 | 4/2001 | Williams et al. | |
| 6,216,045 B1 | 4/2001 | Black et al. | |
| 6,249,707 B1 | 6/2001 | Kohnen et al. | |
| 6,251,115 B1 | 6/2001 | Williams et al. | |
| 6,263,230 B1 | 7/2001 | Haynor et al. | |
| 6,273,877 B1 | 8/2001 | West et al. | |
| 6,309,401 B1 | 10/2001 | Redko et al. | |
| 6,321,123 B1 | 11/2001 | Morris et al. | |
| 6,371,943 B1 | 4/2002 | Racz et al. | |
| 6,415,187 B1 | 7/2002 | Kuzma et al. | |
| 6,456,874 B1 | 9/2002 | Hafer et al. | |
| 6,516,807 B1 | 2/2003 | Panescu et al. | |
| 6,522,932 B1 | 2/2003 | Kuzma et al. | |
| 6,529,774 B1 | 3/2003 | Greene | |
| 6,549,812 B1 | 4/2003 | Smits | |
| 6,553,264 B2 | 4/2003 | Redko et al. | |
| 6,554,809 B2 | 4/2003 | Aves | |
| 6,556,873 B1 | 4/2003 | Smits | |
| 6,704,605 B2 | 3/2004 | Soltis et al. | |
| 6,718,211 B2 | 4/2004 | Smits | |
| 6,733,500 B2 | 5/2004 | Kelley et al. | |
| 6,741,893 B2 | 5/2004 | Smits | |
| 6,745,079 B2 | 6/2004 | King | |
| 6,754,539 B1 | 6/2004 | Erickson et al. | |
| 6,758,854 B1 | 7/2004 | Butler et al. | |
| 6,805,676 B2 | 10/2004 | Klint | |
| 6,836,687 B2 | 12/2004 | Kelley et al. | |
| 6,895,283 B2 | 5/2005 | Erickson et al. | |
| 6,901,289 B2 | 5/2005 | Dahl et al. | |
| 6,902,547 B2 | 6/2005 | Ayes et al. | |
| 6,934,589 B2 | 8/2005 | Sundquist et al. | |
| 6,970,747 B2 | 11/2005 | Kokones et al. | |
| 6,980,863 B2 | 12/2005 | van Venrooij et al. | |
| 6,981,314 B2 | 1/2006 | Black et al. | |
| 6,999,819 B2 | 2/2006 | Swoyer et al. | |
| 7,020,531 B1 | 3/2006 | Colliou et al. | |
| 7,022,109 B1 | 4/2006 | Ditto | |
| 7,047,082 B1 | 5/2006 | Schrom et al. | |
| 7,051,419 B2 | 5/2006 | Schrom et al. | |
| 7,069,083 B2 | 6/2006 | Finch et al. | |
| 7,090,661 B2 | 8/2006 | Morris et al. | |
| 7,146,222 B2 | 12/2006 | Boling | |
| 7,153,307 B2 | 12/2006 | Scribner et al. | |
| 7,181,288 B1 | 2/2007 | Rezai et al. | |
| 7,184,838 B2 | 2/2007 | Cross, Jr. | |
| 7,184,840 B2 | 2/2007 | Stolz et al. | |
| 7,184,842 B2 | 2/2007 | Seifert et al. | |
| 7,187,982 B2 | 3/2007 | Seifert et al. | |
| 7,191,018 B2 | 3/2007 | Gielen et al. | |
| 7,206,642 B2 | 4/2007 | Pardo et al. | |
| 7,241,283 B2 | 7/2007 | Putz | |
| 7,270,650 B2 | 9/2007 | Morris et al. | |
| 7,299,095 B1 | 11/2007 | Barlow et al. | |
| 7,359,755 B2 | 4/2008 | Jones et al. | |
| 7,363,076 B2 | 4/2008 | Yun et al. | |
| 7,379,776 B1 | 5/2008 | Chitre et al. | |
| 7,383,090 B2 | 6/2008 | O'Brien et al. | |
| 7,386,341 B2 | 6/2008 | Hafer et al. | |
| 7,421,297 B2 | 9/2008 | Giftakis et al. | |
| 7,425,142 B1 | 9/2008 | Putz | |
| 7,499,755 B2 | 3/2009 | Cross, Jr. | |
| 7,546,164 B2 | 6/2009 | King | |
| 7,590,454 B2 | 9/2009 | Garabedian et al. | |
| 7,604,644 B2 | 10/2009 | Schulte et al. | |
| 7,627,380 B2 | 12/2009 | Podhajsky et al. | |
| 7,640,064 B2 | 12/2009 | Swoyer | |
| 7,684,873 B2 | 3/2010 | Gerber | |
| 7,797,057 B2 | 9/2010 | Harris | |
| 7,805,188 B2 | 9/2010 | Brushey | |
| 7,881,806 B2 | 2/2011 | Horrigan et al. | |
| 7,904,149 B2 | 3/2011 | Gerber | |
| 7,922,738 B2 | 4/2011 | Eichmann et al. | |
| 8,000,805 B2 | 8/2011 | Swoyer et al. | |
| 8,010,207 B2 | 8/2011 | Smits et al. | |
| 8,014,873 B2 | 9/2011 | Jones et al. | |
| 8,019,439 B2 | 9/2011 | Kuzma et al. | |
| 8,036,756 B2 | 10/2011 | Swoyer et al. | |
| 8,060,207 B2 | 11/2011 | Wallace et al. | |
| 8,078,280 B2 | 12/2011 | Sage | |
| 8,108,052 B2 | 1/2012 | Boling | |
| 8,224,459 B1 | 7/2012 | Pianca et al. | |
| 8,326,439 B2 | 12/2012 | Boling et al. | |
| 8,494,652 B2 | 7/2013 | Cantlon et al. | |
| 8,548,601 B2 | 10/2013 | Chinn et al. | |
| 8,634,934 B2 | 1/2014 | Kokones et al. | |
| 8,712,533 B2 | 4/2014 | Alataris et al. | |
| 8,731,671 B2 | 5/2014 | Rodby et al. | |
| 8,805,519 B2 | 8/2014 | Parker et al. | |
| 9,308,022 B2 | 4/2016 | Chitre et al. | |
| 2001/0014820 A1 | 8/2001 | Gielen et al. | |
| 2001/0016765 A1 | 8/2001 | Gielen et al. | |
| 2001/0023368 A1 | 9/2001 | Black et al. | |
| 2001/0025192 A1 | 9/2001 | Gerber et al. | |
| 2001/0027336 A1 | 10/2001 | Gielen et al. | |
| 2002/0022872 A1 | 2/2002 | Gielen et al. | |
| 2002/0022873 A1 | 2/2002 | Erickson et al. | |
| 2002/0042642 A1 | 4/2002 | Gerber | |
| 2002/0052640 A1 | 5/2002 | Bigus et al. | |
| 2002/0128700 A1 | 9/2002 | Cross | |
| 2002/0173718 A1 | 11/2002 | Frisch et al. | |
| 2002/0198568 A1 | 12/2002 | Hafer et al. | |
| 2003/0199948 A1 | 10/2003 | Kokones et al. | |
| 2003/0199949 A1 | 10/2003 | Pardo | |
| 2003/0199951 A1 | 10/2003 | Pardo et al. | |
| 2003/0199952 A1 | 10/2003 | Stolz et al. | |

(56) References Cited

U.S. PATENT DOCUMENTS

| | | |
|---|---|---|
| 2003/0199953 A1 | 10/2003 | Stolz et al. |
| 2003/0220677 A1 | 11/2003 | Doan et al. |
| 2004/0015133 A1 | 1/2004 | Karim |
| 2004/0024440 A1 | 2/2004 | Cole |
| 2004/0087877 A1 | 5/2004 | Besz et al. |
| 2004/0088033 A1 | 5/2004 | Smits et al. |
| 2004/0088034 A1 | 5/2004 | Smits et al. |
| 2004/0093053 A1 | 5/2004 | Gerber et al. |
| 2004/0162601 A1 | 8/2004 | Smits |
| 2004/0186544 A1 | 9/2004 | King |
| 2004/0215301 A1 | 10/2004 | Lokhoff et al. |
| 2004/0215305 A1 | 10/2004 | Sage |
| 2004/0215307 A1 | 10/2004 | Michels et al. |
| 2004/0243206 A1 | 12/2004 | Tadlock |
| 2005/0004638 A1 | 1/2005 | Cross |
| 2005/0021119 A1 | 1/2005 | Sage et al. |
| 2005/0049486 A1 | 3/2005 | Urquhart et al. |
| 2005/0049663 A1 | 3/2005 | Harris et al. |
| 2005/0049664 A1 | 3/2005 | Harris et al. |
| 2005/0065588 A1 | 3/2005 | Zhao et al. |
| 2005/0090885 A1 | 4/2005 | Harris et al. |
| 2005/0096718 A1 | 5/2005 | Gerber et al. |
| 2005/0107861 A1 | 5/2005 | Harris et al. |
| 2005/0137646 A1 | 6/2005 | Wallace et al. |
| 2005/0138791 A1 | 6/2005 | Black et al. |
| 2005/0138792 A1 | 6/2005 | Black et al. |
| 2005/0182420 A1 | 8/2005 | Schulte et al. |
| 2005/0182421 A1 | 8/2005 | Schulte et al. |
| 2005/0182422 A1 | 8/2005 | Schulte et al. |
| 2005/0182424 A1 | 8/2005 | Schulte et al. |
| 2005/0182425 A1 | 8/2005 | Schulte et al. |
| 2005/0192655 A1 | 9/2005 | Black et al. |
| 2005/0203599 A1 | 9/2005 | Garabedian et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0283216 A1 | 12/2005 | Pyles |
| 2005/0288759 A1 | 12/2005 | Jones et al. |
| 2006/0030918 A1 | 2/2006 | Chinn et al. |
| 2006/0041295 A1 | 2/2006 | Osypka |
| 2006/0089691 A1 | 4/2006 | Kaplan et al. |
| 2006/0089692 A1 | 4/2006 | Cross et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0168805 A1 | 8/2006 | Hegland et al. |
| 2006/0200218 A1 | 9/2006 | Wahlstrand |
| 2006/0206118 A1 | 9/2006 | Kim et al. |
| 2006/0206183 A1 | 9/2006 | Pyles et al. |
| 2006/0247749 A1 | 11/2006 | Colvin |
| 2006/0253182 A1 | 11/2006 | King |
| 2006/0264122 A1 | 11/2006 | Aman et al. |
| 2007/0050004 A1 | 3/2007 | Swoyer et al. |
| 2007/0055332 A1 | 3/2007 | Swoyer |
| 2007/0100408 A1 | 5/2007 | Gerber |
| 2007/0135881 A1 | 6/2007 | Vilims |
| 2007/0191903 A1 | 8/2007 | Bruinstroop |
| 2007/0213795 A1 | 9/2007 | Bradley et al. |
| 2007/0249901 A1 | 10/2007 | Ohline et al. |
| 2007/0255364 A1 | 11/2007 | Gerber et al. |
| 2007/0255365 A1 | 11/2007 | Gerber et al. |
| 2007/0255366 A1 | 11/2007 | Gerber et al. |
| 2007/0255367 A1 | 11/2007 | Gerber et al. |
| 2007/0255369 A1 | 11/2007 | Bonde et al. |
| 2007/0255370 A1 | 11/2007 | Bonde et al. |
| 2007/0255371 A1 | 11/2007 | Bonde et al. |
| 2007/0261115 A1 | 11/2007 | Gerber et al. |
| 2008/0103569 A1 | 5/2008 | Gerber |
| 2008/0103572 A1 | 5/2008 | Gerber |
| 2008/0103576 A1 | 5/2008 | Gerber |
| 2008/0103578 A1 | 5/2008 | Gerber |
| 2008/0103579 A1 | 5/2008 | Gerber |
| 2008/0103580 A1 | 5/2008 | Gerber |
| 2008/0132926 A1 | 6/2008 | Eichmann et al. |
| 2008/0156333 A1 | 7/2008 | Galpern et al. |
| 2008/0183257 A1 | 7/2008 | Imran et al. |
| 2008/0183259 A1 | 7/2008 | Bly et al. |
| 2008/0262430 A1* | 10/2008 | Anderson .......... A61B 17/3415 604/164.1 |
| 2008/0300651 A1 | 12/2008 | Gerber et al. |
| 2009/0048638 A1 | 2/2009 | Rey et al. |
| 2009/0069803 A1 | 3/2009 | Starkebaum |
| 2009/0125060 A1 | 5/2009 | Rivard et al. |
| 2009/0132017 A1 | 5/2009 | Erickson et al. |
| 2009/0204173 A1 | 8/2009 | Fang et al. |
| 2009/0216306 A1 | 8/2009 | Barker |
| 2009/0299444 A1 | 12/2009 | Boling |
| 2009/0319013 A1 | 12/2009 | Boling et al. |
| 2010/0063356 A1 | 3/2010 | Smith |
| 2010/0094115 A1 | 4/2010 | Pond, Jr. et al. |
| 2010/0094116 A1 | 4/2010 | Silverstein |
| 2010/0114283 A1 | 5/2010 | King |
| 2010/0179562 A1 | 7/2010 | Linker et al. |
| 2010/0204569 A1 | 8/2010 | Burnside et al. |
| 2010/0256696 A1 | 10/2010 | Schleicher et al. |
| 2010/0267265 A1 | 10/2010 | Dilmaghanian |
| 2010/0274314 A1 | 10/2010 | Alataris et al. |
| 2010/0274315 A1 | 10/2010 | Alataris et al. |
| 2010/0274326 A1 | 10/2010 | Chitre et al. |
| 2010/0280570 A1 | 11/2010 | Sturm et al. |
| 2010/0286551 A1 | 11/2010 | Harley et al. |
| 2010/0292769 A1 | 11/2010 | Brounstein et al. |
| 2010/0305670 A1 | 12/2010 | Hall et al. |
| 2010/0318165 A1 | 12/2010 | Harris |
| 2010/0324414 A1 | 12/2010 | Harley et al. |
| 2010/0324570 A1 | 12/2010 | Rooney et al. |
| 2011/0071593 A1 | 3/2011 | Parker et al. |
| 2011/0106100 A1 | 5/2011 | Bischoff |
| 2011/0160568 A1 | 6/2011 | Seeley et al. |
| 2011/0178573 A1 | 7/2011 | Nguyen-Stella et al. |
| 2011/0202097 A1 | 8/2011 | Bonde et al. |
| 2011/0224682 A1 | 9/2011 | Westlund et al. |
| 2011/0245903 A1 | 10/2011 | Schulte et al. |
| 2012/0232626 A1 | 9/2012 | Daglow |
| 2013/0066331 A1 | 3/2013 | Chitre et al. |
| 2013/0066411 A1 | 3/2013 | Thacker et al. |
| 2013/0116754 A1 | 5/2013 | Sharma et al. |
| 2013/0261697 A1 | 10/2013 | Parker |
| 2014/0303685 A1 | 10/2014 | Rosenberg et al. |
| 2016/0059006 A1 | 3/2016 | Doan et al. |
| 2016/0302827 A1 | 10/2016 | Chitre et al. |
| 2016/0354609 A1 | 12/2016 | Parker et al. |
| 2016/0360993 A1 | 12/2016 | Thacker et al. |

FOREIGN PATENT DOCUMENTS

| | | |
|---|---|---|
| EP | 0709111 A2 | 5/1996 |
| WO | WO-9003824 A1 | 4/1990 |
| WO | WO-03013650 A1 | 2/2003 |
| WO | WO-2003011361 A2 | 2/2003 |
| WO | WO-2009129329 A1 | 10/2009 |

OTHER PUBLICATIONS

Cook Medical, Lead Management, "Byrd Dilator Sheaths—Telescoping Polypropylene," http://www.cookmedical.com/lm/dataSheet.do?id=5453, 2012, 2 pages.

Cook Medical, Lead Management, "Byrd Dilator Sheaths—Telescoping PTFE," http://www.cookmedical.com/lm/dataSheet.do?id=5455, 2012, 1 page.

Intrel® Model 7490 / 7491 Extensions for Spinal Cord Stimulation (SCS), Medtronic Neuro, Minneapolis, MN 1984, 9 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Malecka et al., "Long-Term Consequences of Endocardial Leads Present in Cardiovascular System," Department of Electrocardiology, Institute of Cardiology, Modern Pacemakers—Present and Future, 2011, 18 pages.

Medtronic, "Physician and Hospital Staff Manual," InterStrim System, ; Neurological Division. 93 pages, undated.

(56) References Cited

OTHER PUBLICATIONS

Kulkarni et al., "A two-layered forward model of tissue for electrical impedance tomography," Physiol Meas., 30(6); pp. 1-24, Jun. 2009.

* cited by examiner

LEAD INSERTION DEVICES AND ASSOCIATED SYSTEMS AND METHODS

The present application is a divisional of U.S. patent application Ser. No. 13/710,341, filed on Dec. 10, 2012, which is incorporated herein by reference in its entirety.

TECHNICAL FIELD

The present technology is directed generally to insertion devices for percutaneously placing patient leads, and associated systems and methods. Insertion devices, and associated systems and methods in accordance with the present technology are suitable for placing multiple leads through a single percutaneous access point.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator (IPG) that is operably coupled to one or more leads that deliver electrical pulses to neurological tissue or muscle tissue. For example, several neurological stimulation systems for spinal cord stimulation (SCS) have cylindrical leads that include a lead body with a circular cross-sectional shape and multiple conductive rings spaced apart from each other at the distal end of the lead body. The conductive rings operate as individual electrodes or contacts to deliver electrical signals to the patient. The SCS leads are typically implanted either surgically or percutaneously through a needle inserted into the epidural space, often with the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In particular, the electrical pulses can generate sensations that mask or otherwise alter the patient's sensation of pain. For example, in many cases, patients report a tingling or paresthesia that is perceived as more pleasant and/or less uncomfortable than the underlying pain sensation. In other cases, the patients can report pain relief without paresthesia or other sensations.

DETAILED DESCRIPTION

The present technology is directed generally to insertion devices and systems and methods for neuromodulation systems, and more specifically to single access or single entrance point insertion systems for implanting spinal cord modulation leads. Several embodiments of the present technology include access systems having insertion needles and multiple dilators. In various embodiments, the insertion needles and dilators are configured in a variety of suitable manners and can be employed independently or together to implant multiple leads through a single percutaneous entry point in a patient. For example, the present technology can include an insertion needle having a cannula, a stylet, and a series of dilators that can operate together to open and expand a single percutaneous entry point in a patient. In other embodiments, the devices, systems and associated methods can have different configurations, components, and/or procedures. Still other embodiments may eliminate particular components and/or procedures. Additionally, the present technology, which includes associated devices, systems, procedures, methods of use, and instructions for steps included in a method of use, may include other embodiments with additional elements or steps, and/or may include other embodiments with or without several of the features or steps shown and described below with reference to FIGS. 1-11. Further, while embodiments presented in FIG. 1 may describe lead implantation in spinal cord stimulation systems, other embodiments of the presented technology are applicable in other fields and/or other neuromodulation settings and/or other surgical lead or tool implantations.

Figure 1:
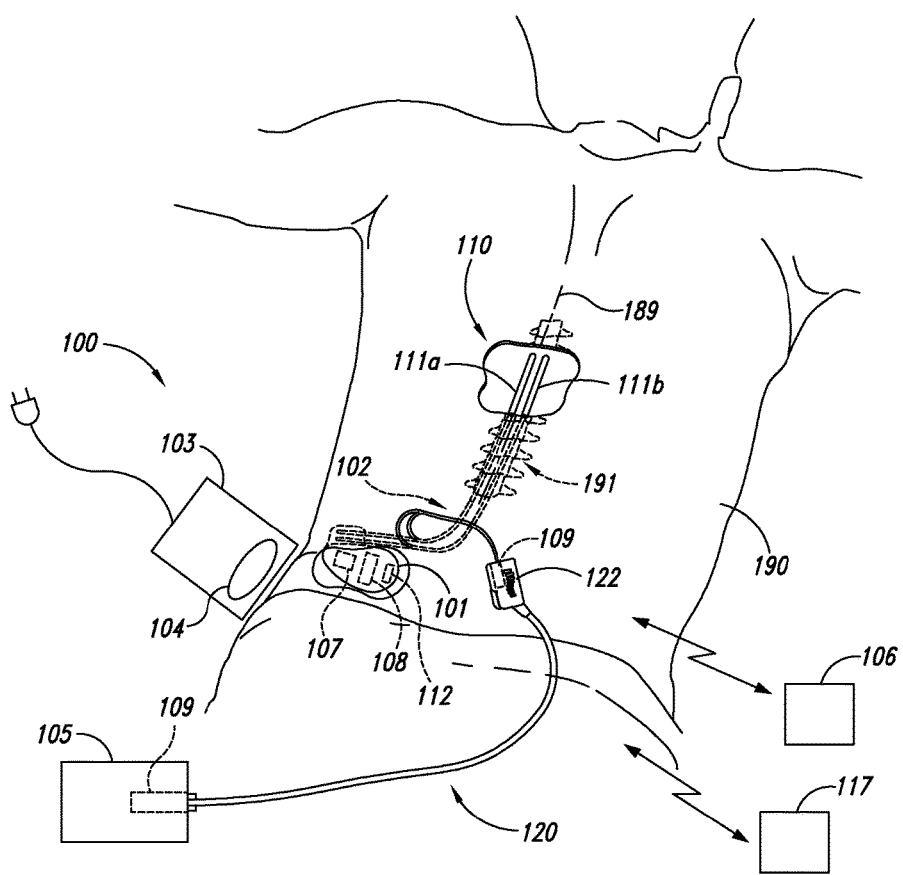
FIG. 1 is a partially schematic illustration of a spinal cord stimulation system positioned to deliver therapeutic signals in accordance with an embodiment of the present technology.

FIG. 1 schematically illustrates a representative patient system 100 for providing relief from chronic pain and/or other conditions, arranged relative to the general anatomy of a patient's spinal cord 191. The overall patient system 100 can include one or more signal delivery devices 110, which may be implanted within a patient 190, typically at or near the patient's spinal cord midline 189, coupled to an implantable pulse generator 101. The signal delivery devices 110 carry features for delivering therapy to the patient 190 after implantation. The pulse generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 111 (identified individually as a first lead 111a and a second lead 111b). As used herein, the terms "lead" and "lead body" include any of a number of suitable substrates and/or support members that carry devices for providing therapy signals to the patient 190. For example, the lead or leads 111 can include one or more electrodes or electrical contacts that direct electrical signals into the patient's tissue, such as to provide for patient pain relief. In other embodiments, the signal delivery devices 110 can include structures other than a lead body (e.g., a paddle) that also direct electrical signals and/or other types of signals to the patient 190.

The pulse generator 101 can transmit therapy signals (e.g., electrical signals) to the signal delivery devices 110 that up-regulate (e.g., stimulate or excite) and/or down-regulate (e.g., block or suppress) target nerves. As used herein, and unless otherwise noted, to "modulate" or provide "modulation" to the target nerves refers generally to having either type of the foregoing effects on the target nerves. The pulse generator 101 can include a machine-readable (e.g., computer-readable) medium containing instructions for generating and transmitting suitable therapy signals. The pulse generator 101 and/or other elements of the system 100 can include one or more processor(s) 107, memory unit(s) 108 and/or input/output device(s) 112. Accordingly, the process of providing electrical signals, providing guidance information for positioning the signal delivery devices 110, and/or executing other associated functions can be performed by computer-executable instructions contained by computer-readable media located at the pulse generator 101 and/or other system components. The pulse generator 101 can include multiple portions, elements, and/or subsystems (e.g., for directing signals in accordance with multiple signal delivery parameters), carried in a single housing, as shown in FIG. 1, or in multiple housings.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

During at least some procedures, an external stimulator or trial modulator 105 can be coupled to the signal delivery devices 110 during an initial procedure, prior to implanting the pulse generator 101. For example, a practitioner (e.g., a physician and/or a company representative) can use the trial modulator 105 to vary therapy parameters provided to the signal delivery devices 110 in real time, and select optimal or particularly efficacious parameters. These parameters can include the location from which the electrical signals are emitted, as well as the characteristics of the electrical signals provided to the signal delivery devices 110. In a typical process, the practitioner uses a cable assembly 120 to temporarily connect the trial modulator 105 to the signal delivery devices 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters, may not be performed.

The pulse generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. Receiving elements 109 can be at least generally similar in structure and function to those described in U.S. patent application Ser. No. 13/291, 985, entitled MEDICAL DEVICE CONTACT ASSEMBLIES FOR USE WITH IMPLANTABLE LEADS, AND ASSOCIATED SYSTEMS AND METHODS, filed Nov. 8, 2011, which is incorporated by reference herein in its entirety. To the extent any of the foregoing patents, patent applications and/or any other materials incorporated herein by reference conflict with the present disclosure, the present disclosure controls.

After a trial period with the trial modulator 105, the practitioner can implant the implantable pulse generator 101 within the patient 190 for longer term treatment. The signal delivery parameters provided by the pulse generator 101 can still be updated after the pulse generator 101 is implanted, via a wireless physician's programmer 117 (e.g., a physician's laptop, physician's remote, etc.) and/or a wireless patient programmer 106 (e.g., a patient's laptop, patient's remote, etc.).

Inserting SCS leads percutaneously can provide a less invasive procedure than direct surgical implantation of the leads. Percutaneous insertion can reduce patient discomfort and recovery time associated with the procedure. In many instances, it is preferable to insert more than one SCS lead at a given treatment location. For example, two cylindrical leads are often positioned proximate to each other at a treatment location. Current percutaneous insertion devices require separate access/entrance points for inserting each individual lead into the epidural space, or other suitable implant location. However, each additional access/entrance point increases patient discomfort and increases the probability of infection. Accordingly, presented herein is a percutaneous implantation system that facilitates implanting multiple SCS leads through a single access/entrance point.

Figure 2:
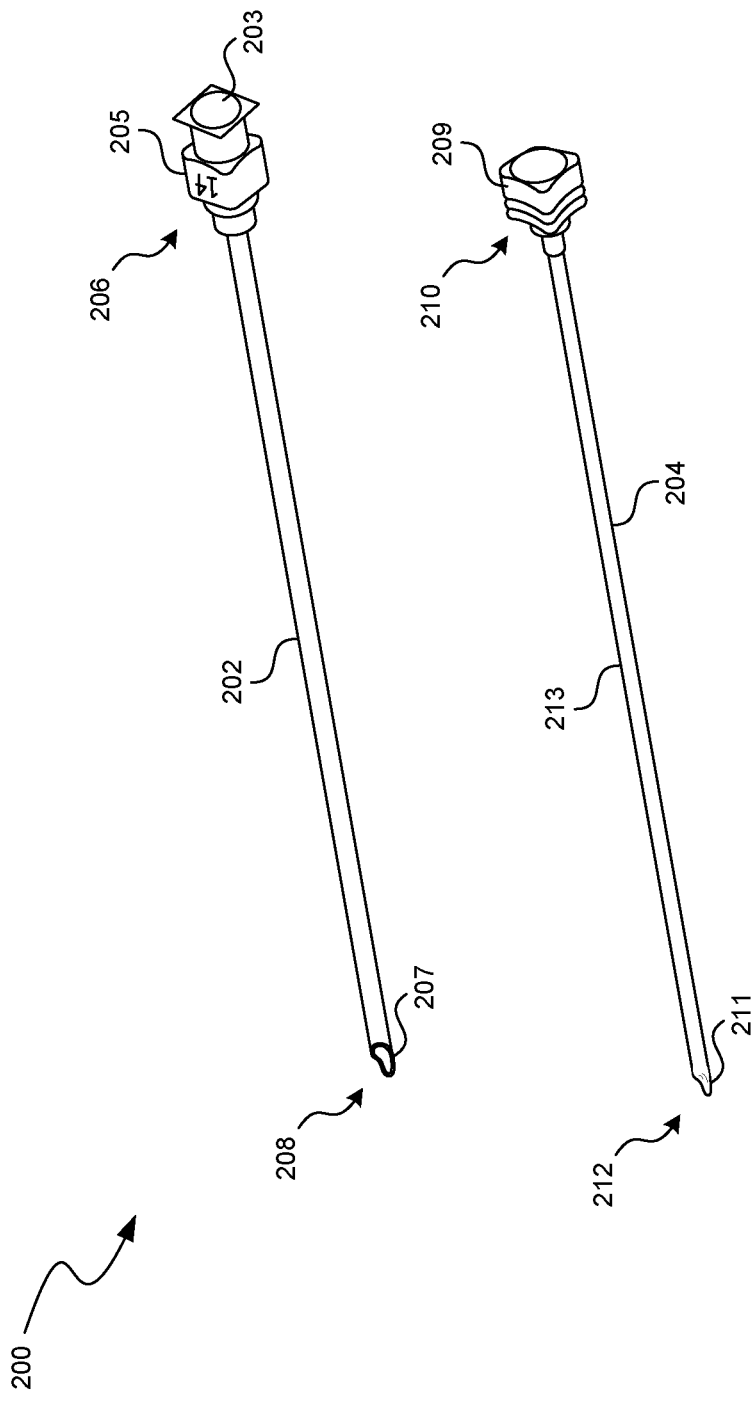
FIGS. 2-4 are isometric views of an insertion needle having a cannula and a stylet configured in accordance with an embodiment of the present technology.
Figure 3:
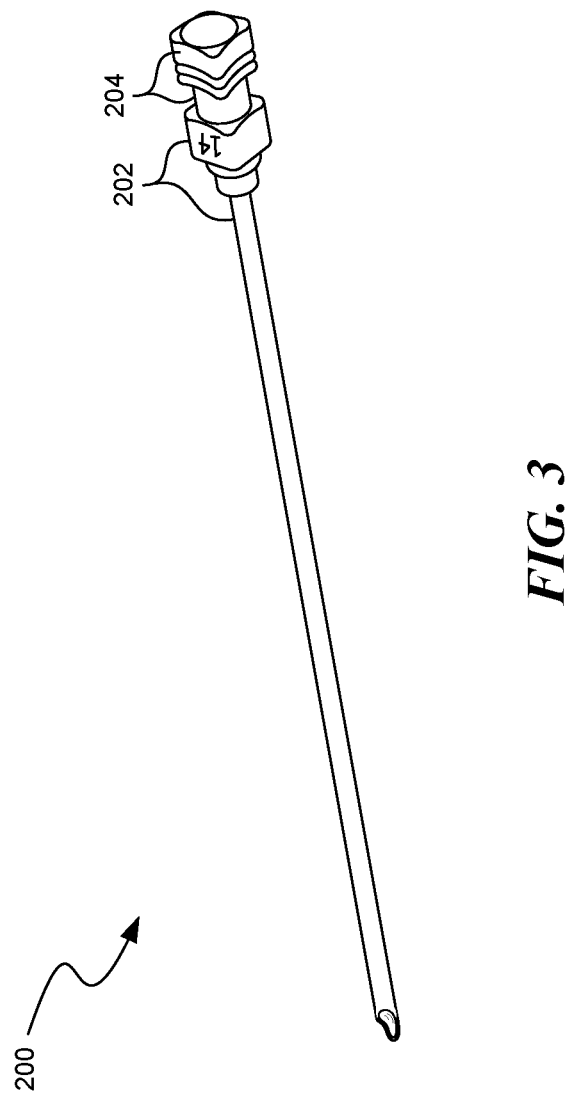
Figure 4:
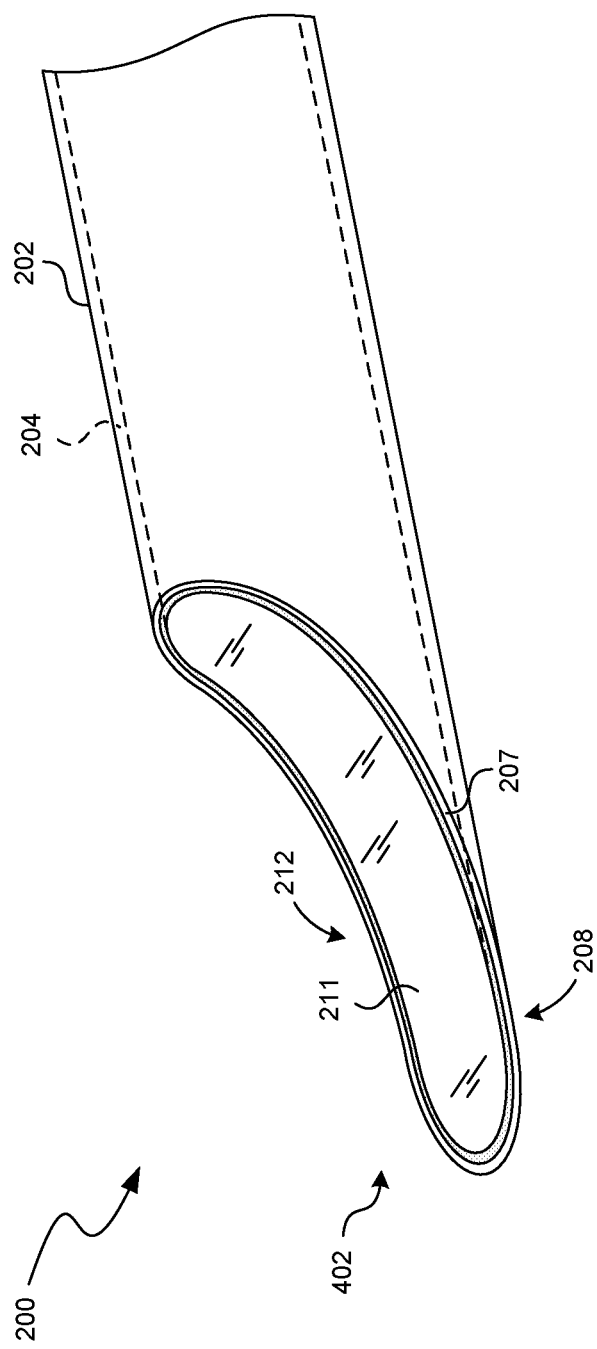

FIGS. 2-4 are isometric views of an insertion needle 200 having a cannula 202 and a stylet 204 configured to implant leads, such as signal delivery devices 111a and/or 111b of FIG. 1, in accordance with an embodiment of the present technology. FIG. 2 illustrates the insertion needle 200 in a disassembled state, with the cannula 202 and the stylet 204 spaced apart from each other. FIGS. 3 and 4 illustrate the insertion needle 200 in an assembled state, with the stylet 204 positioned within, and removeably coupled to, the cannula 202, as described further below. Referring first to FIG. 2, the cannula 202 includes a lumen 203 that extends from a proximal end 206 to a distal end 208. The proximal end 206 can include a cannula hub 205 and the distal end 208 can have a beveled cannula tip 207.

Similarly, the stylet 204 extends from a proximal end 210 having a stylet hub 209 to a distal end 212 having a beveled stylet tip 211. The stylet 204 in the illustrated embodiment includes a solid cylinder 213 that extends from the stylet hub 209 to the beveled stylet tip 211. However, in some embodiments, the stylet 204 can include a lumen and/or other non-solid portions. In one embodiment, the stylet 204 includes a removable hub 209. As further described below, inclusion of a removable hub 209 allows the stylet 204 to serve both its primary function of aiding in the insertion of the cannula 202, as well as a secondary function of acting as a first dilator or dilator guide.

The cannula 202 in the illustrated embodiments of FIGS. 2-4 is a 14 gauge cannula. In some embodiments, the cannula 202 can be of a size in the range of 12 gauge to 18 gauge. In other embodiments, the cannula 202 can be larger than 12 gauge, or smaller than 18 gauge. The lumen 203 of the cannula 202 can be configured to receive the stylet 204 for assembling the insertion needle 200. For example, the distal end 212 of the stylet 204 can be inserted into the cannula lumen 203 at the proximal end 206 of the cannula 202. The stylet 204 can be advanced within the lumen 203 until the stylet hub 209 contacts and/or engages the cannula hub 205, as shown in FIG. 3. The beveled stylet tip 211 can be shaped to match the beveled cannula tip 207. For example, when the stylet 204 is fully inserted into the cannula 202, the beveled cannula tip 207 and the beveled stylet tip 211 can align to form a generally uniform beveled insertion needle tip 402, as shown in FIG. 4. Additionally, in some embodiments, the cannula hub 205 (FIG. 2) can releasably engage with the stylet hub 209 to removeably couple the stylet 204 to the cannula 202. In one embodiment, the cannula hub 205 mates with the stylet hub 209 in only one position so as to align the stylet tip 211 with the cannula tip 207, thereby establishing the uniform beveled insertion needle tip 402.

The beveled insertion needle tip 402 can be shaped in a variety of suitable manners. For example, in the illustrated embodiment, the beveled insertion needle tip 402 is generally "shovel" shaped (e.g., curved). In other embodiments, the beveled insertion needle tip 402 can include a beveled end that is straight, rather than curved. In still other embodiments, the insertion needle tip 402 can include other suitable shapes or configurations, e.g., compound curves. Further, the stylet tip 211 and the cannula tip 207 may be configured such that their combined surface area reduces the amount of directed pressure the beveled insertion needle tip 402 exerts on a tissue-needle interface (i.e., the pressure on the patient tissue at the point of insertion of the needle 200).

In operation, an assembled insertion needle 200 can be inserted into a patient to create a percutaneous entry point. During insertion, the solid stylet 204 can "block" the cannula lumen 203 and reduce the possibility of "needle hole" injuries and/or other potential complications. For example, the beveled insertion needle tip 402 with the solid stylet 204 can act as a sharp wedge that opens up a percutaneous entry point in a patient without "coring" a hole in the patient. I.e., the solid stylet 204 can effectively close off the entrance to the lumen 203 at the distal end 208 of the cannula 202, thereby reducing the possibility for the cannula 202 to cut a "core" of skin from the patient. After the percutaneous entry point has been created, the stylet 204 can be removed from the cannula 202. For example, the stylet 204 can be extracted from the cannula 202 by grasping and pulling the stylet hub 209 while holding the cannula hub 205 (FIGS. 2 and 3). Removing the stylet 204 can provide for expanding a percutaneous entry point, as described below. Alternatively, the stylet hub 209 may be removed, and the cannula 202 may be withdrawn over the stylet 204. With the stylet hub 209 removed, the stylet 204 may serve as an initial dilator or dilator guide for further opening of the percutaneous entry point.

Figure 5A:
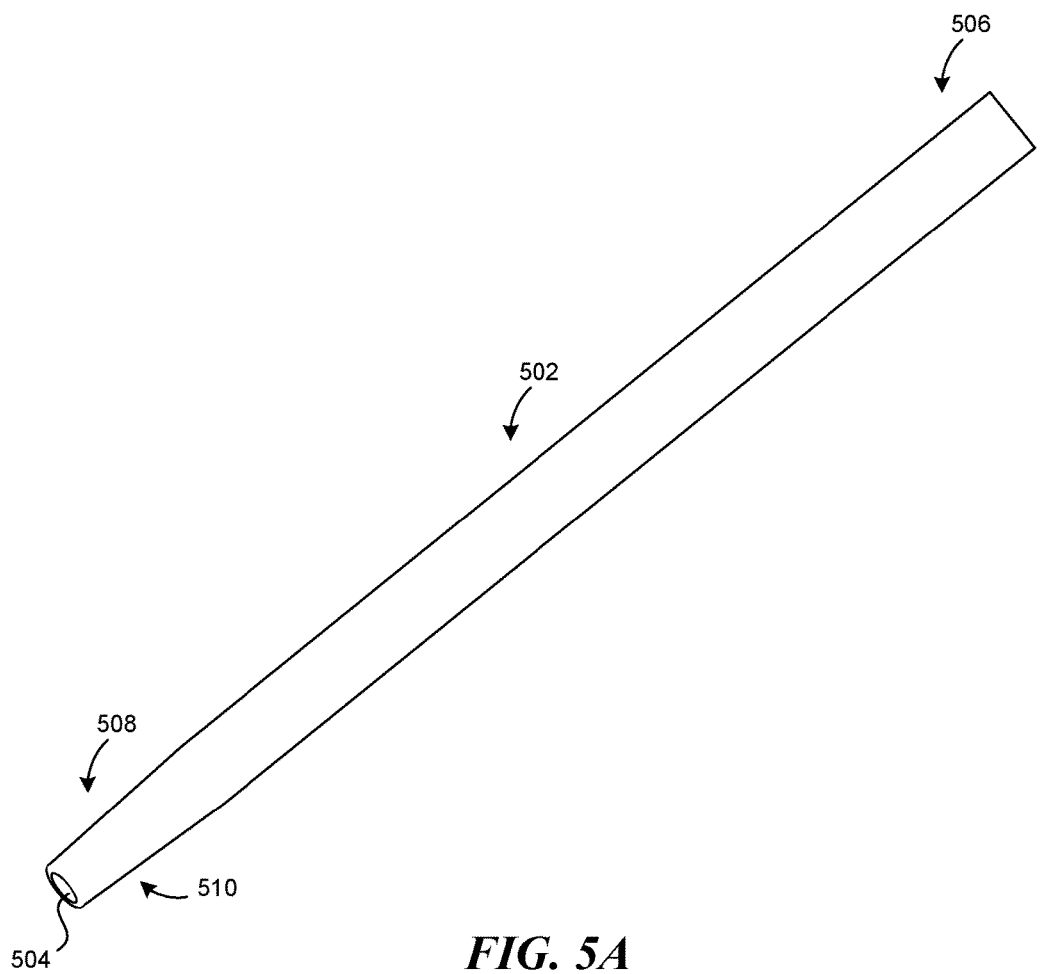
FIGS. 5A and 5B are isometric and cross-sectional side views, respectively, of a dilator configured in accordance with another embodiment of the present technology.
Figure 5B:
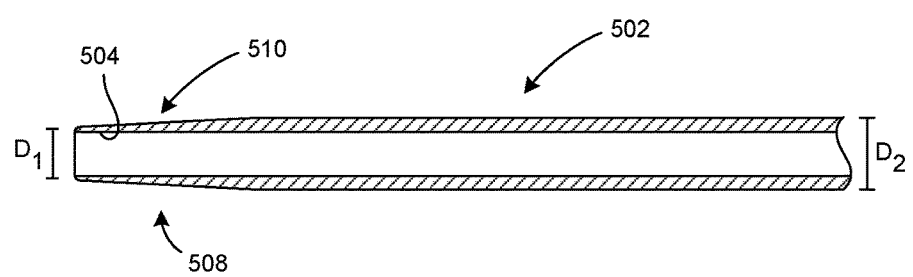

FIGS. 5A and 5B are isometric and cross-sectional side views, respectively, of a dilator 502 configured in accordance with an embodiment of the present technology. The dilator 502 can be used in conjunction with the cannula 202 and the stylet 204 shown in FIGS. 2-4, as will be described further below. In the illustrated embodiment, the dilator 502 includes a lumen 504 extending through the dilator 502 from a proximal end 506 to a distal end 508. The distal end 508 of the dilator 502 can include a tapered section 510, and the outside diameter of the dilator 502 can vary from a first diameter D1 at the distal end 508 to a second diameter D2, greater than the first diameter D1, at the proximal end 506.

The dilator 502 can be configured to be received within the cannula 202. For example, the second diameter D2 can be less than the width of the cannula lumen 203 (FIG. 2), such that the dilator 502 can be inserted into the lumen 203. The dilator 502 may also be configured to be received over the stylet 213. For example, the first and second diameter D1 and D2 can be greater than the outer diameter of the stylet 213. The dilator 502 can be constructed from a variety of suitable materials (e.g., polypropylene, polytetrafluoroethylene (PTFE), Delrin, high density polyethylene (HDPE), low density polyethylene (LDPE), or Teflon) and can be constructed to have varying amounts of flexibility. For example, in some embodiments the dilator 502 can be flexible and soft (e.g., bendable along a longitudinal axis and relatively pliable), and in other embodiments the dilator 502 can be rigid and stiff (e.g., unbendable about a longitudinal axis and relatively unpliable). Additionally, the dilator 502 can be constructed with materials that are loaded with barium, e.g., polypropylene loaded with barium or Teflon loaded with barium. In embodiments having barium, the dilator 502 can be radiopaque, which can be beneficial for radiographic imaging techniques.

Figure 6A:
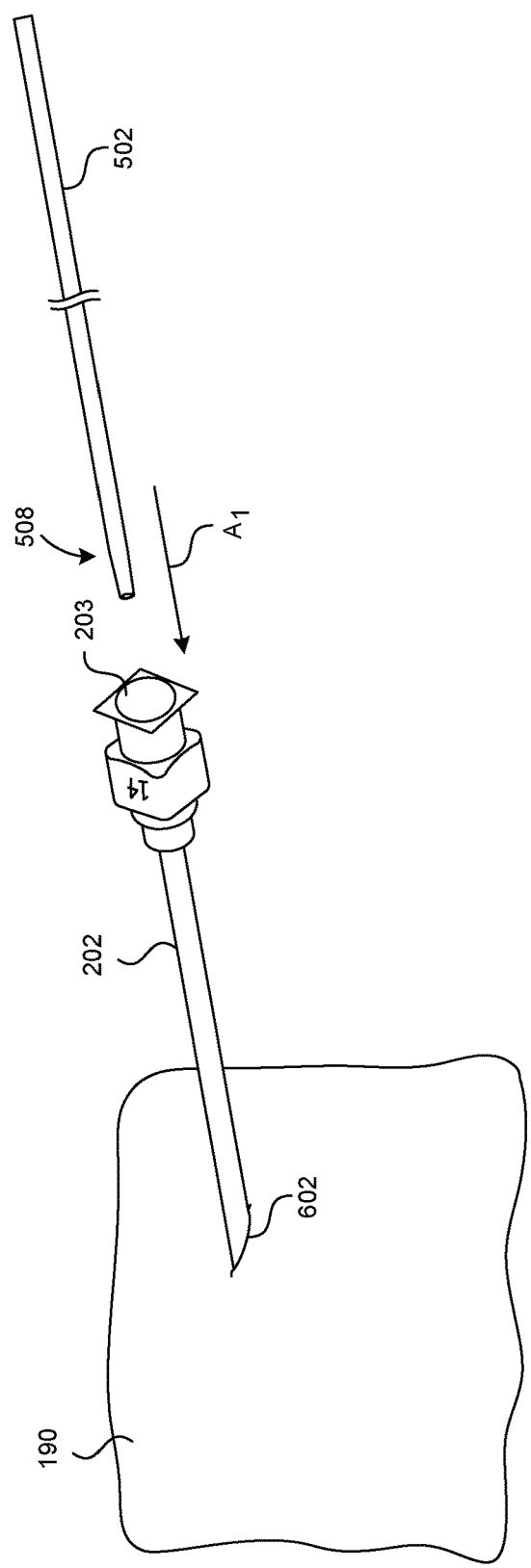
FIGS. 6A and 6B are isometric views of a dilator and a cannula during a procedure in accordance with an embodiment of the present technology.
Figure 6B:
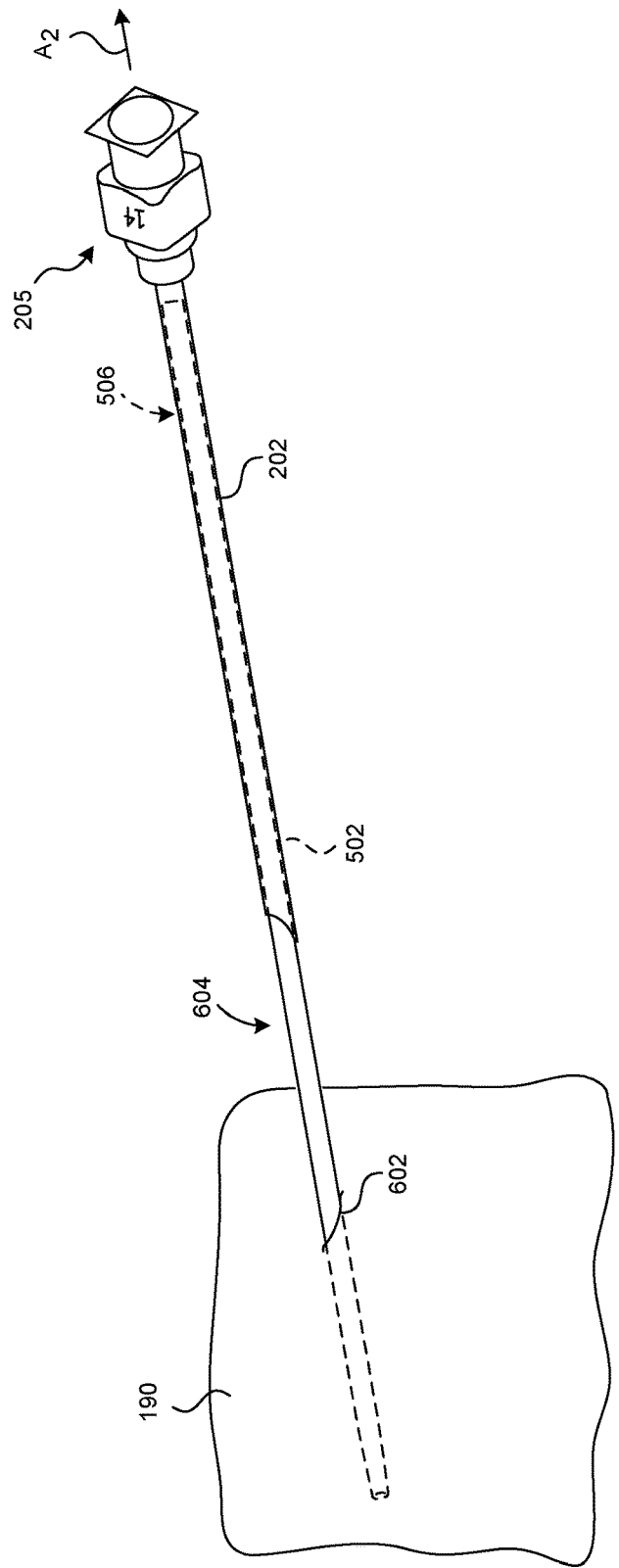

FIGS. 6A and 6B are isometric views of the dilator 502 and the cannula 202 during a procedure in accordance with an embodiment of the present technology. As shown in FIG. 6A, the practitioner inserts the cannula 202 through a percutaneous entry point 602 into a patient 190, to position a distal end (not visible) of the cannula 202 beneath the patient's skin. The dilator 502 in FIG. 6A is positioned for insertion into the patient 190 through the cannula lumen 203. For example, after removal of the stylet 204 (FIGS. 2-4), the distal end 508 of the dilator 502 can be inserted into the lumen 203, and the distal end 508 can be advanced in the direction of arrow $A_1$ past the percutaneous entry point 602. Accordingly, the dilator 502 can extend through the percutaneous entry point 602 within the lumen 203. It should be noted that the dilator 502 is of a length that is greater than the length of the cannula 202. After the dilator 502 has been positioned to extend through the percutaneous entry point 602, the cannula 202 can be removed, as illustrated in FIG. 6B. In the illustrated embodiment of FIG. 6B, the dilator 502 extends through the percutaneous entry point 602. The cannula 202 can be removed by grasping and pulling the cannula hub 205 in the direction of arrow $A_2$ until the cannula 202 is separated from the dilator 502. In the illustrated embodiment, the dilator 502 has an overall length that is longer than the length of the cannula 202. In such embodiments, the proximal end 506 of the dilator 502 can be held while the cannula 202 is pulled in the direction of $A_2$ to remove the cannula 202 from the patient 190. As the cannula 202 is moved in the direction of $A_2$, past the percutaneous entry point 602, a portion 604 of the dilator 502 is exposed near the percutaneous entry point 602. The practitioner can hold this portion 604 of the dilator 502 in place as he/she moves the cannula 202 further in the direction of $A_2$ and separates the cannula 202 from the dilator 502.

Figure 7A:
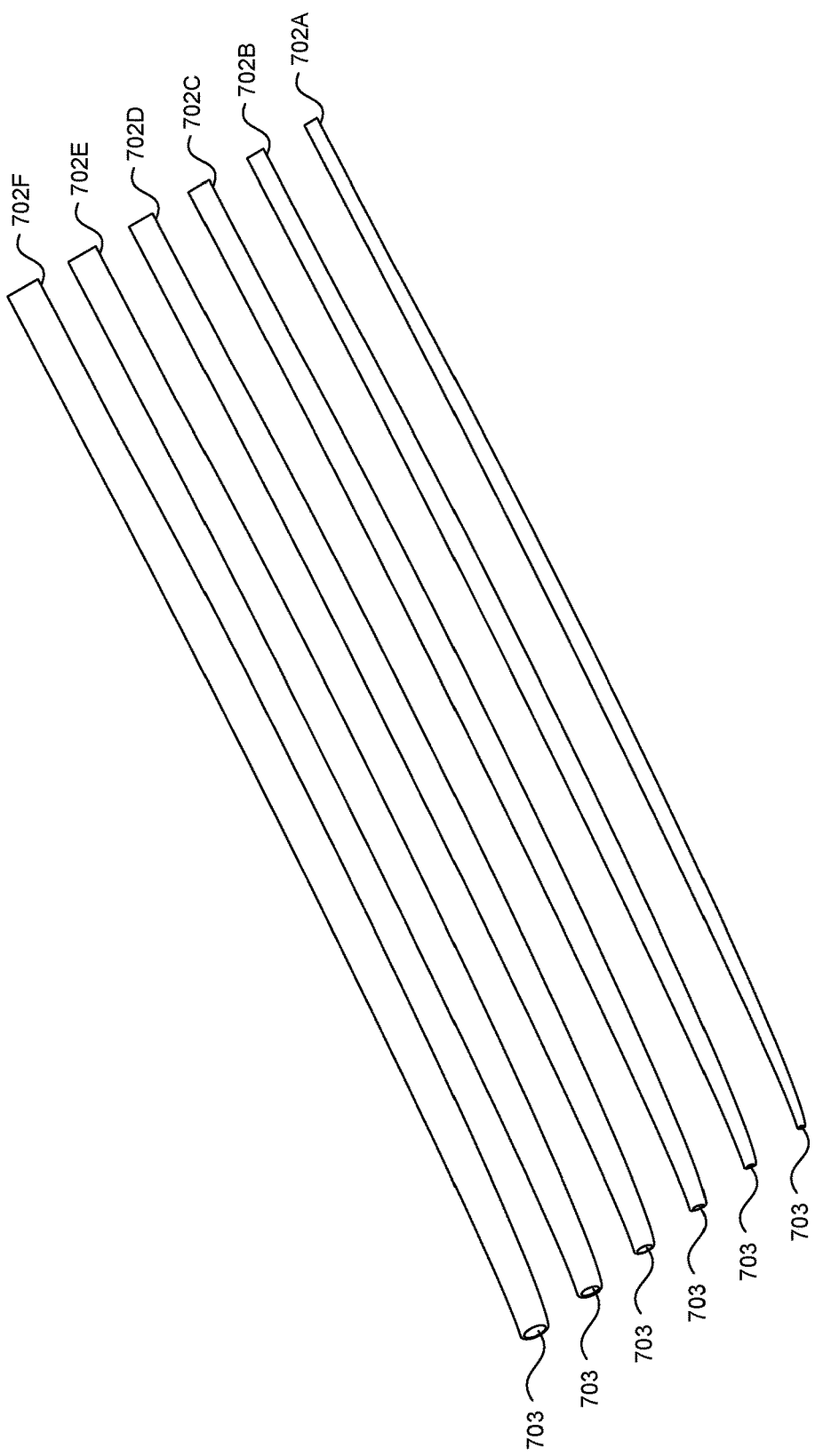
FIGS. 7A and 7B are isometric views of a set of dilators configured in accordance with a further embodiment of the present technology.
Figure 7B:
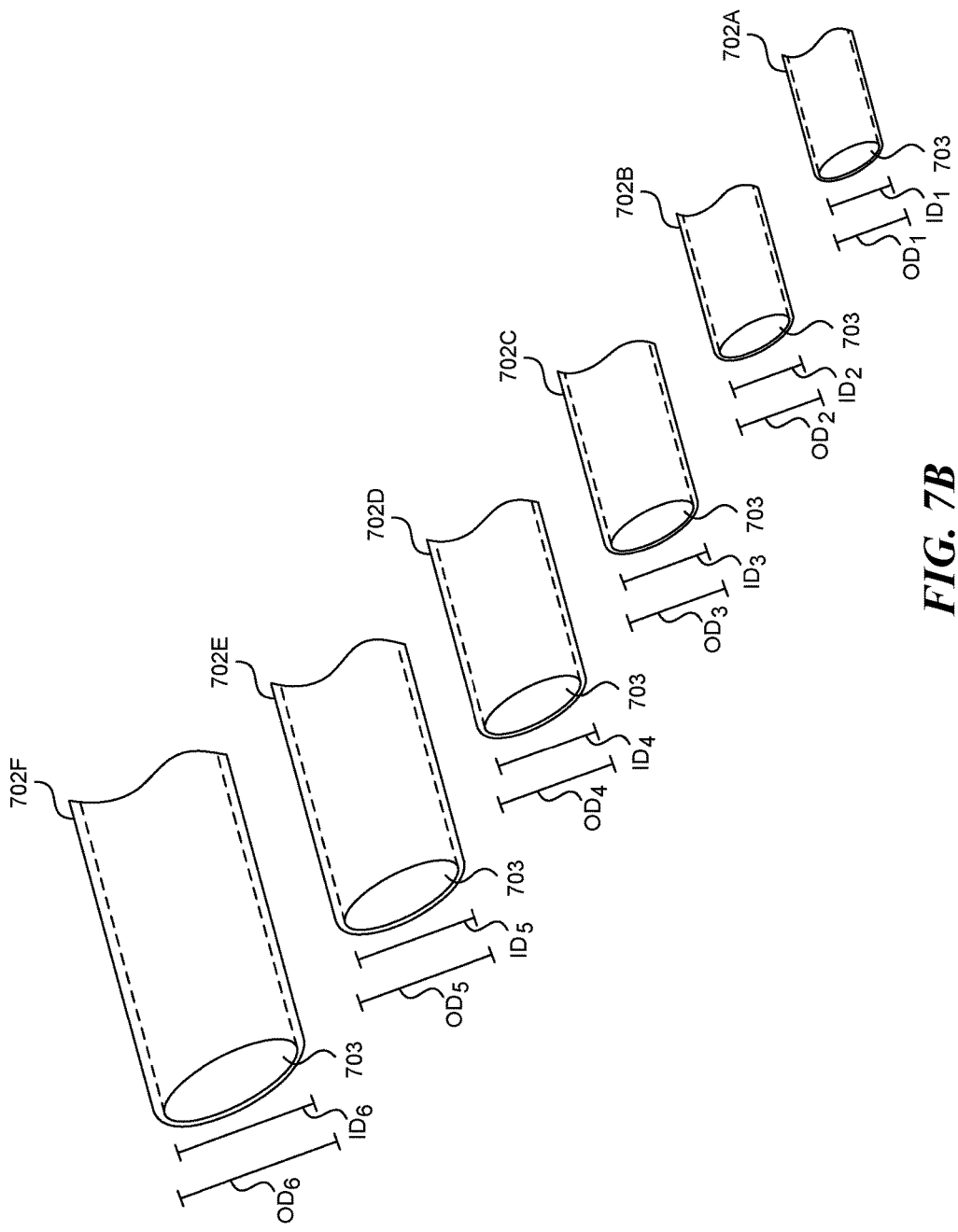

FIGS. 7A and 7B are isometric views of a set of dilators 702 (identified individually as first-sixth dilators 702a-702f) configured in accordance with an embodiment of the present technology. FIG. 7A illustrates the entire length of each of the dilators 702, while FIG. 7B is a close-up view illustrating a distal end of each of the dilators 702. Referring to FIGS. 7A and 7B, together, each of the dilators 702 can be at least generally similar in structure and function to the dilator 502 shown in FIGS. 5A-6B. In the illustrated embodiments, the dilators 702 have corresponding increasing outside diameters OD (identified individually as first-sixth outside diameters OD1-OD6). Additionally, the dilators 702 include corresponding lumens 703 having increasing inside diameters ID (identified individually as first-sixth inside diameters ID1-ID6). In a particular embodiment, the sixth dilator 702*f* is the last or final dilator, while in other embodiments, the dilator set 702 can include any suitable number of dilators greater than or equal to two. The second dilator 702*b* through the sixth dilator 702*f* can be configured to fit over the corresponding next smallest dilator 702 (e.g., the first dilator 702*a* through the fifth dilator 702*e*). For example, the second dilator 702*b* includes an inside diameter ID2 that is larger than the outside diameter OD1 of the first dilator 702*a*, such that the second dilator 702*b* can slide over the first dilator 702*a*.

Figure 8:
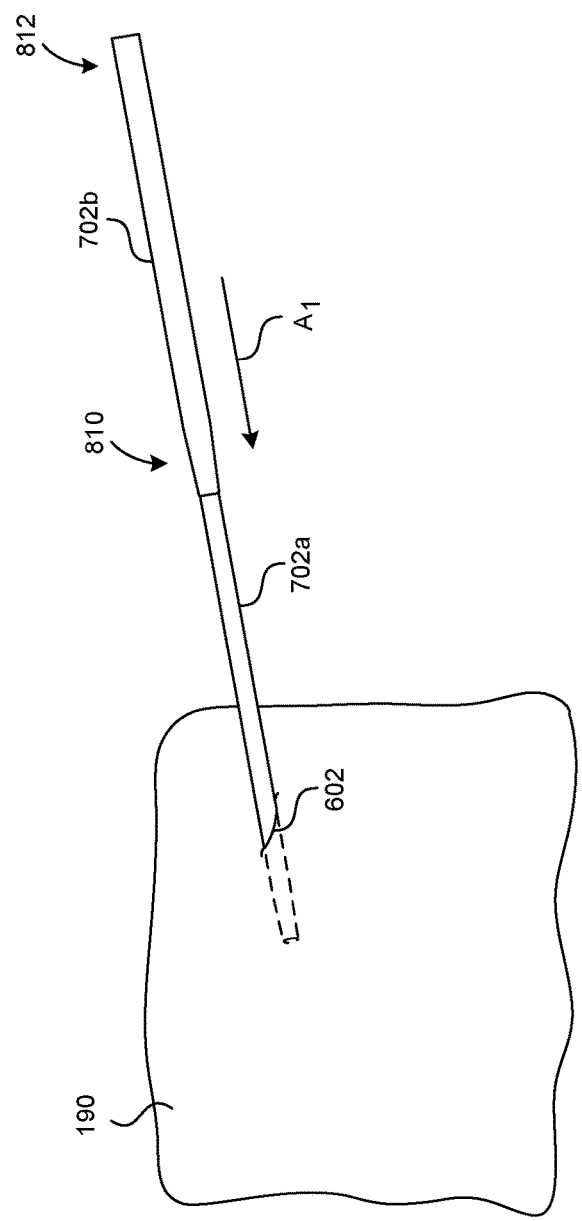
FIG. 8 is an isometric view of a first dilator and a second dilator during a procedure in accordance with an embodiment of the present technology.

FIG. 8 is an isometric view of the first dilator 702*a* and the second dilator 702*b* during a procedure in accordance with an embodiment of the present technology. As discussed above, the second or other subsequent dilator 702*b* can be configured to fit over the first or other preceding dilator 702*a*. In the illustrated embodiment, the first dilator 702*a* is positioned to extend through the percutaneous entry point 602 into the patient 190. The first dilator 702*a* can be inserted into the patient 190 in a manner at least generally similar to that described above with respect to the dilator 502 shown in FIGS. 5A-6B. The second dilator 702*b* can be positioned over the first dilator 702*a* and maneuvered to expand the percutaneous entry point 602. For example, the second dilator 702*b* can be advanced in the direction of arrow $A_1$ along the first dilator 702*a*. A tapered portion 810 of the second dilator 702*b* can act to expand the percutaneous entry point 602 as the second dilator 702*b* is moved further in the direction of arrow $A_1$. As the second dilator 702*b* is moved further in the direction of arrow A1, a proximal end (not shown) of the first dilator 702*a* can extend out of a distal end 812 of the second dilator 702*b*. The practitioner can grasp the proximal end of the first dilator 702*a* and remove it from the patient 190 and from within the second dilator 702*b*. This process can be halted after two dilators, or repeated with any suitable number of additional dilators, e.g., the third dilator 702*c* through the final dilator 702*f*, to incrementally expand the percutaneous entry point 602. The expansion of the percutaneous entry point 602 obtained by increasing the outside diameters ODs of successive dilators 702 corresponds to an increase in the inside diameters IDs of the lumens 703 of the dilators 702. This can produce a desired final inside diameter ID large enough to accommodate inserted signal delivery devices (e.g., leads).

In one embodiment, the final dilator 702 can be selected to have an inside diameter ID that simultaneously accommodates two leads, e.g., side by side. For example, a particular lead can have an approximate external diameter of 4 French (1.33 mm). Accordingly, a dilator 702 having an inside diameter ID slightly larger than 8 French (2.66 mm), e.g., a dilator having a 9 French (3 mm) inside diameter ID, can be the final dilator 702 that is inserted through a percutaneous entry point, thereby allowing two 4 French leads to be inserted through the dilator lumen 703 in a side by side configuration. In other embodiments, dilators 702 having lumens 703 with different sized inside diameters ID can be chosen to accommodate the insertion of two or more devices having larger or smaller dimensions than the 4 French leads discussed above. In some embodiments, dilators 702 can include lumens 703 having inside diameters IDs chosen to accommodate two leads having different external diameters. For example, in one embodiment, a dilator 702 having an 8 French inside diameter ID can accommodate a first lead having a 3 French external diameter and a second lead having a 4 French external diameter. Additionally, although the external diameter of the leads discussed herein can include a diameter of a circular cross-section, the term external diameter, and/or diameter, can include a variety of other dimensions.

Although the illustrated embodiment of FIG. 7 includes six dilators 702, other embodiments can include additional or fewer dilators 702. For example, in some embodiments, two dilators 702 can be sufficient to expand a percutaneous entry point to the desired inside diameter ID. Accordingly, in some embodiments only the first dilator 702*a* and the second dilator 702*b* may be used. In other embodiments, a cannula having a lumen sized to receive the third dilator 702*c* may be used, and the third dilator 702*c* may be used with the fourth dilator 702*d* to expand the percutaneous entry point. In some embodiments, a set of dilators may be provided together as a group, and the appropriate dilators 702 may be selected for a particular procedure. Additionally, in the illustrated embodiment of FIG. 7, the length of each dilator 702 is at least approximately equal. In other embodiments, the length of each dilator 702 can decrease as the diameter increases. In this manner, when a subsequent dilator 702 is positioned over a preceding dilator 702 and advanced to the same depth within a patient, a proximal end of the preceding dilator 702 remains exposed. Accordingly, a physician, surgeon, or other medical practitioner can grasp the proximal end of the preceding dilator 702 to remove it from within the patient 190, without needing to insert the subsequent dilator 702 deeper than the preceding dilator 702.

Figure 9:
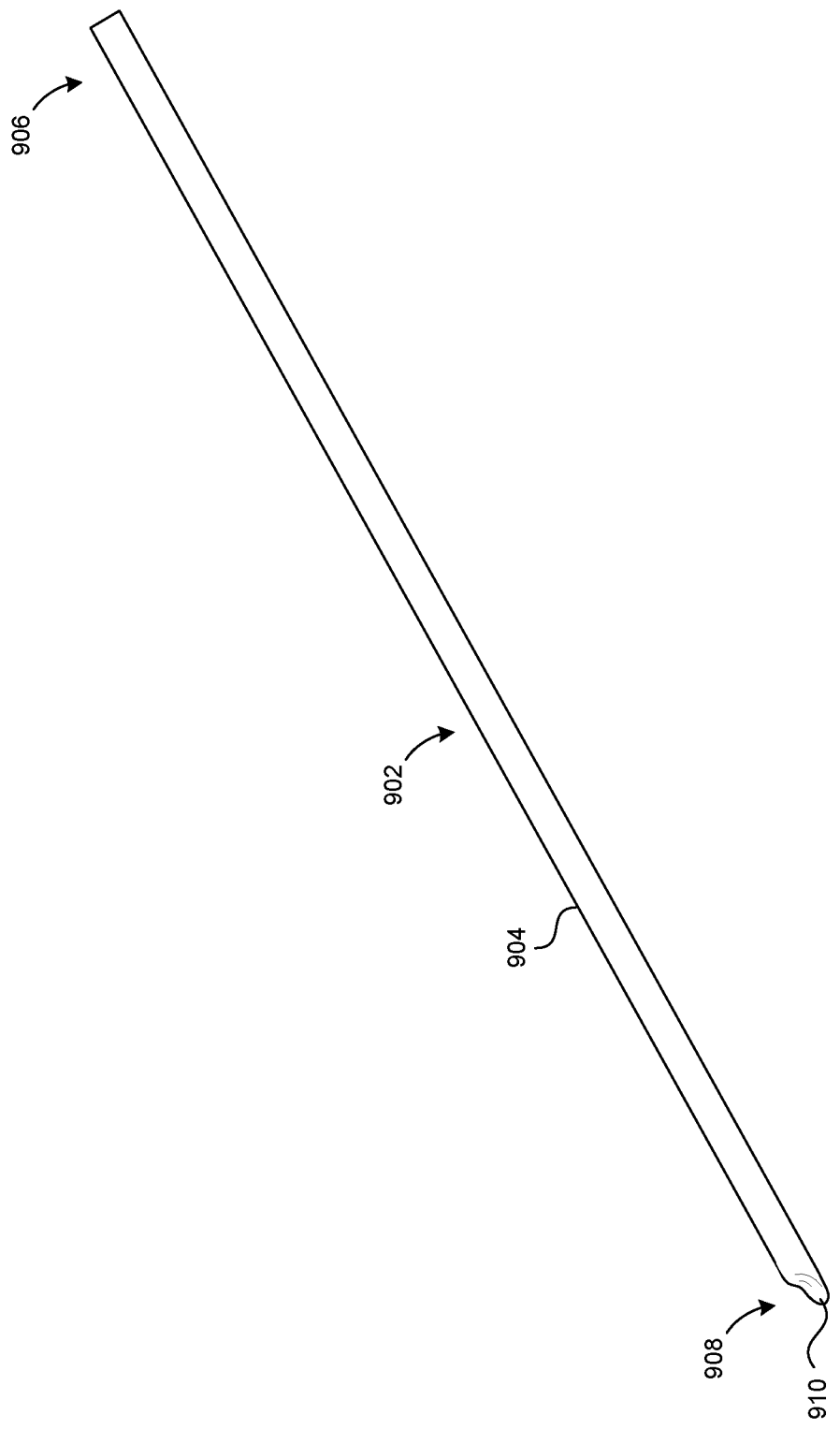
FIG. 9 is an isometric view of a dilator configured in accordance with another embodiment of the present technology.

FIG. 9 is an isometric view of a dilator 902 configured in accordance with a further embodiment of the present technology. The dilator 902 can be at least generally similar in structure and function to the dilators 502 and 702 described above with respect to FIGS. 5A to 8. For example, the dilator 902 can be constructed from a variety of suitable materials, including, e.g., polypropylene, PTFE, and Teflon. However, in the illustrated embodiment, the dilator 902 includes a solid tube 904 extending from a proximal end 906 to a distal end 908. Additionally, the distal end 908 includes a shovel-shaped beveled dilator tip 910. The beveled dilator tip 910 can be shaped to match the beveled stylet tip 211 (FIG. 4). In one embodiment, the dilator 902 can be used in place of the stylet 204 to create a percutaneous entry point. For example, the dilator 902 can be positioned within the cannula 202 (FIGS. 2-4) with the beveled dilator tip 910 aligning with the beveled cannula tip 207. In operation, the practitioner can simultaneously insert the cannula 202 and the dilator 902 into a patient to create the percutaneous entry point, with the solid core of the dilator 902 blocking the cannula lumen 203, e.g., to prevent tissue coring. Accordingly, the dilator 902 can reduce the possibility for injuries in a manner at least generally similar to those described above with respect to the stylet 204. In some embodiments, the dilator 902 can include an aperture or lumen, or other non-solid portion (e.g., a blind hole), small enough to not cause coring.

The dilator 902 can also reduce the number of steps required to position a dilator 702 having a desired inside diameter ID. For example, in contrast to the procedure described above with respect to FIGS. 2-6B, after the percutaneous entry point has been created with the cannula 202 and the dilator 902, the cannula 202 can be removed from the patient, leaving the dilator 902 extending through the percutaneous entry point. One of the dilators 702 can subsequently be positioned over the dilator 902 and advanced into the patient. Accordingly, the dilator 902 can obviate the need to replace the stylet 204 with a first dilator 702a prior to inserting a second dilator 702b.

The dilator 902 in FIG. 9 includes a proximal end 906 having no hub. However, in some embodiments, a removable hub can be added to the dilator 902 at the proximal end 906 to facilitate creating a percutaneous entry point. The removable hub can operably couple the dilator 902 to the cannula 202 and/or can aid in maintaining the alignment of the beveled dilator tip 910 with the beveled cannula tip 207. The removable hub can be separated from the dilator 902 after the percutaneous entry point has been created, thereby allowing the cannula 202 to be removed over the dilator 902. In other embodiments, other devices, structures or methods can be used to maintain the alignment of the cannula 202 and the dilator 902 relative to each other as the practitioner creates the percutaneous entry point. For example, the cannula hub 205 can include a mechanism that can removeably couple the dilator 902 to the cannula 202. In one embodiment, this can include a tube clamp (e.g., a tube clamp having a quick release mechanism). In other embodiments, other securing mechanisms can be used to temporarily secure the dilator 902 within the cannula 202 (e.g., male and female threads). Furthermore, in some embodiments, the dilator 902 can include a compressible hub at the proximal end 906. The compressible hub can assist in maintaining the position of the dilator 902 within the cannula 202 and/or aligning the beveled dilator tip 910 and the beveled cannula tip 207, and can also be compressed to fit through the cannula lumen 203. Although various embodiments described herein include descriptions of methods of use, other embodiments can include instructing one or more steps included in a method of use.

Figure 10:
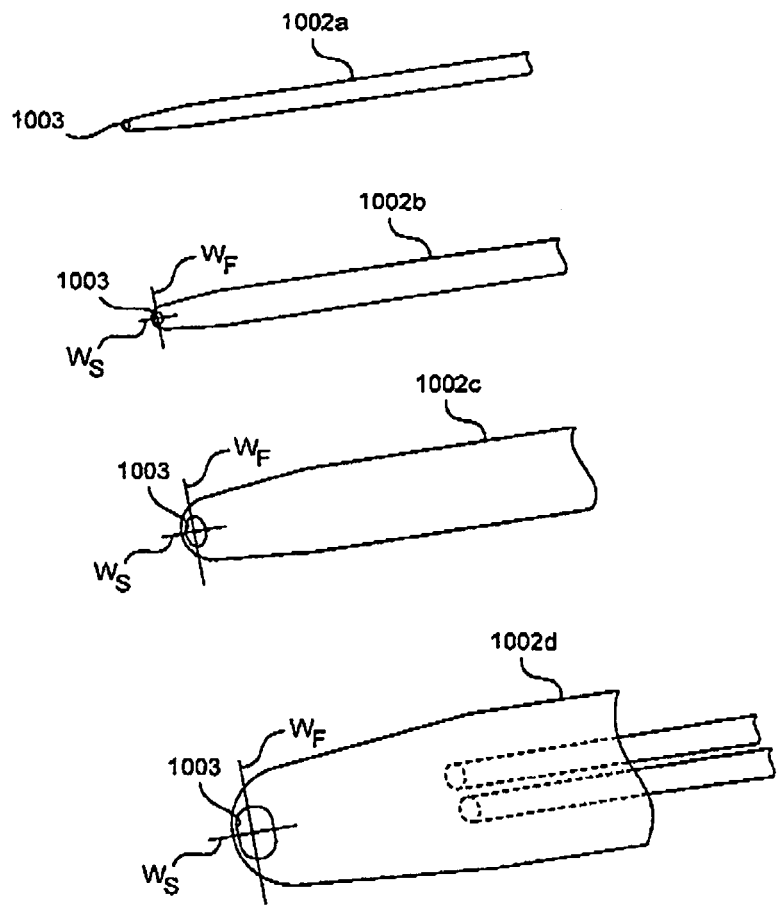
FIG. 10 is an isometric view of a set of dilators configured in accordance with a further embodiment of the present technology.

FIG. 10 is an isometric view of a set of dilators 1002 (identified individually as a first-fourth (e.g., final) dilator 1002a-1002d) configured in accordance with an embodiment of the present technology. Similar to the dilators 702 described above, the dilators 1002 can be used to expand a percutaneous entry point to provide for the insertion of other medical devices. For example, the dilators 1002 include lumens 1003 that increase in size from the first dilator 1002a to the final dilator 1002d. However, the cross-sectional shape of the dilators 1002 and the lumens 1003 in the second dilator 1002b through the final dilator 1002d is not circular, but elliptical. In particular, the second-fourth dilators 1002b-1002d, and their respective lumens 1003, have widths along a first cross-sectional axis $W_F$ that are longer than the widths along a second cross-sectional axis $W_S$. The elliptical shape of the second-final dilator 1002b-1002d can allow one or more medical devices to be inserted through a smaller percutaneous entry point. In one embodiment, the lumen 1003 of the final dilator 1002d can be sized to allow two cylindrical leads to pass through simultaneously. For example, in a particular embodiment, the width of the dilator lumen 1003 along the first cross-sectional axis $W_F$ for the final dilator 1002d can be approximately 9 French (3 mm) to accommodate two 4 French (1.33 mm) leads side by side along the first cross-sectional axis $W_F$. With the leads positioned side by side along the first cross-sectional axis $W_F$, the dilator 1002d can have a smaller width along the second cross-sectional axis $W_S$. For example, in one embodiment, the lumen 1003 can have a width along the second cross-sectional axis $W_S$ of approximately 5 French (1.66 mm). Accordingly, the dilator 1002d can have a smaller outside dimension, and thereby produce a smaller percutaneous entry than that produced by a dilator having a round cross-sectional area. Although the example above describes dimensions designed to accommodate two 4 French (1.33 mm) leads, in other embodiments, the size of the lumens 1003 can be smaller or larger than this example to provide a desired size for the insertion of two or more medical devices having larger or smaller dimensions. Additionally, although the illustrated embodiment includes four dilators 1002, other embodiments may include more or fewer dilators 1002.

The dilators 1002 can be employed in a manner at least generally similar to the dilators 702 and 902 described above. For example, after a percutaneous entry point has been created with the cannula 202 and the stylet 204, the stylet 204 can be removed, the first dilator 1002a can be inserted into the cannula 204, the cannula 204 can be removed from the patient, and the second dilator 1002b through the final dilator 1002d can be sequentially inserted into the patient over the preceding dilator to expand the percutaneous entry point. Alternatively, the dilator 902 can be used in conjunction with the cannula 202 (as described above) and the second dilator 1002b through the final dilator 1002d can be sequentially inserted into the patient over the preceding dilator to expand the percutaneous entry point.

Figure 11:
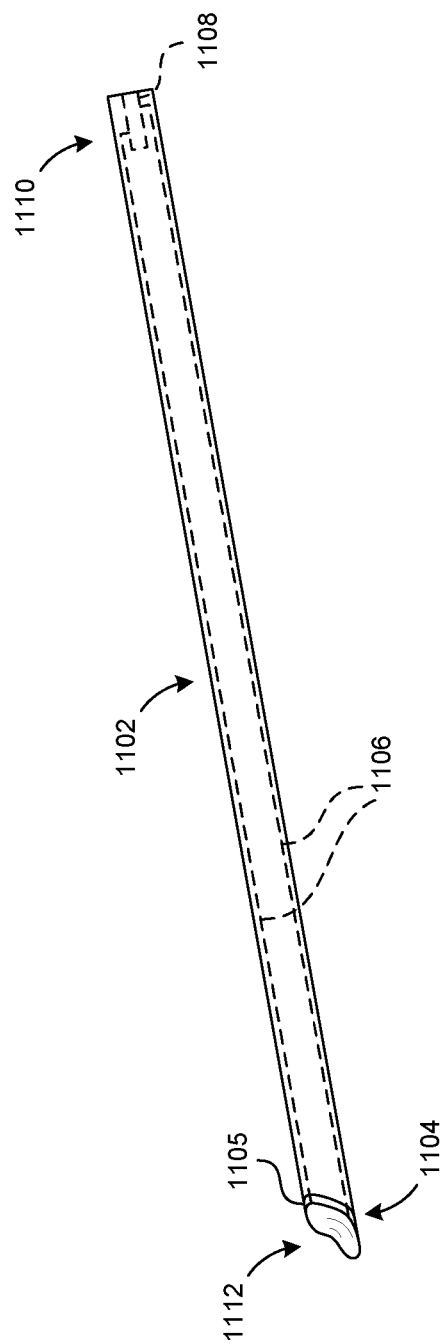
FIG. 11 is a partially schematic isometric view of a dilator having a mapping contact configured in accordance with another embodiment of the present technology.

FIG. 11 is a partially schematic isometric view of a dilator 1102 having a mapping contact 1104 configured in accordance with another embodiment of the present technology. The dilator 1102 can be at least generally similar in structure and function to the dilator 1002 described above with respect to FIG. 10. However, the dilator 1102 can be used in combination with the cannula 202 to both create a percutaneous entry point and to identify penetration of a patient's dura. In the illustrated embodiment, the mapping contact 1104 includes a metallic band 1105 that extends around the circumference of the dilator 1102 at a distal end 1112 of the dilator 1102. A pair of conducting lines 1106 can connect the contact 1104 to a plug 1108 at a proximal end 1110 of the dilator 1102. A connector (not shown) can be inserted into the plug 1108 to connect the dilator 1102 to a monitoring device that can monitor the impedance in an electrical circuit that includes the contact 1104. Changes in the impedance of the electrical circuit that occur as the contact 1104 enters a patient's dura can provide an indication of intrathecal penetration. The dilator 1102 can be configured in a variety of suitable manners, including in manners at least generally similar to those described in U.S. patent application Ser. No. 12/895,438, entitled SYSTEMS AND METHODS FOR DETECTING INTRATHECAL PENETRATION, filed Sep. 30, 2011, the entirety of which is incorporated herein by reference. Although the illustrated embodiment of FIG. 11 includes a metallic band 1105, the mapping contact 1104 can include a variety of suitable conductive materials, e.g., conductive polymers.

Percutaneous implantation systems in accordance with the present technology can provide several benefits. For example, by reducing the number of access points necessary for a percutaneous implantation, embodiments in accordance with the present technology can reduce the amount of anesthetic required, reduce infections, and reduce the need for antibiotics. Additionally, the percutaneous implantation systems described herein can reduce the number of steps and the amount of time required for insertion procedures. For example, while existing procedures often require a guidewire to be inserted to provide guidance for an expansion device, embodiments of the present technology can eliminate this step. The embodiment described above with respect to FIGS. 2-6B, for example, provides for the insertion of the dilator 502 through the lumen 203 of the cannula 502, without requiring a guidewire. Removing the steps required for the insertion and the eventual withdrawal of a guidewire reduces the time required to perform a given implantation. Furthermore, reducing the number of devices inserted into a patient can reduce the chance of patient injury (e.g., accidental spinal taps).

Access systems in accordance with the present technology can provide for the insertion of high frequency modulation systems, including those described in the following co-owned patent applications: U.S. patent application Ser. No. 12/264,836, filed Nov. 4, 2008, and titled MULTI-FREQUENCY NEURAL TREATMENTS AND ASSOCIATED SYSTEMS AND METHODS; U.S. patent application Ser. No. 12/765,747, filed Apr. 22, 2010, and titled SELECTIVE HIGH-FREQUENCY SPINAL CORD MODULATION FOR INHIBITING PAIN WITH REDUCED SIDE EFFECTS AND ASSOCIATED SYSTEMS AND METHODS; and U.S. patent application Ser. No. 13/607,617, filed Sep. 7, 2012, and titled SELECTIVE HIGH FREQUENCY SPINAL CORD MODULATION FOR INHIBITING PAIN, INCLUDING CEPHALIC AND/OR TOTAL BODY PAIN WITH REDUCED SIDE EFFECTS, AND ASSOCIATED SYSTEMS AND METHODS. The above referenced patent applications are incorporated herein by reference in their entireties.

ADDITIONAL EMBODIMENTS

In one embodiment, there is provided a system for implanting a plurality of medical devices in a patient through a single percutaneous entry point, the system comprising: (a) a cannula having a cannula lumen extending therethrough, the cannula lumen having an inside diameter; (b) a first dilator having an outside diameter smaller than the inside diameter of the cannula lumen, the first dilator positionable within the cannula lumen to prevent coring upon insertion of the cannula and the first dilator into the patient to produce the percutaneous entry point; and (c) at least one additional dilator, including a final dilator, wherein each additional dilator includes a dilator lumen having an inside diameter larger than an outside diameter of a preceding dilator, and wherein each additional dilator is positionable over a preceding dilator to expand the percutaneous entry point. The system may further comprise two leads, each lead having a diameter, and wherein the final dilator includes a lumen having an inside diameter greater than the sum of the diameters of the leads. The final dilator may include a lumen having an elliptical cross-sectional shape, wherein a diameter along a first axis of the dilator lumen is greater than the sum of the diameters of the leads.

A distal end of the cannula can include a beveled tip having a shovel shape and a distal end of the first dilator can include a beveled tip having a shovel shape positioned to align with the beveled tip of the cannula.

The first dilator can include a beveled tip and a removable hub, wherein the cannula includes a beveled tip, and wherein the removable hub is positioned to align the beveled tip of the cannula with the beveled tip of the dilator.

The first dilator can include a mapping contact positioned to detect intrathecal penetration.

In another embodiment, a patient system comprises: (a) two leads positionable to deliver electrical therapy signals, each lead having a diameter; (b) an insertion needle including a cannula and a stylet, wherein the cannula includes a cannula lumen having an inside diameter, and the stylet includes an outside diameter smaller than the inside diameter of the cannula lumen; (c) a first dilator having an outside diameter smaller than the inside diameter of the cannula lumen and positionable within the cannula lumen; and (d) at least one additional dilator, including a final dilator, wherein each additional dilator includes a dilator lumen having an inside diameter larger than an outside diameter of a preceding dilator, wherein each additional dilator is positionable over a preceding dilator to expand a percutaneous entry point, and wherein the final dilator includes a dilator lumen having an inside diameter or width greater than the sum of the diameters of the leads. The final dilator can include an elliptical cross-sectional shape, wherein the width is a first width along a first cross-sectional axis, and wherein the lumen of the final dilator includes a second width along a second cross-sectional axis that is smaller than the first width and larger than the diameter of either of the two leads. The distal end of the cannula and the distal end of the first dilator can form a beveled tip having a shovel shape.

In yet another embodiment, there is provided a method for treating a patient, comprising: (a) inserting or instructing insertion of a preceding dilator into a patient; (b) positioning or instructing positioning of and advancement of a subsequent dilator over the preceding dilator and into the patient; (c) removing or instructing removal of the preceding dilator from the patient; (d) inserting or instructing insertion of at least two medical devices side by side into the subsequent dilator; and (e) advancing or instructing advancement of the medical devices into the patient. The method may further comprise: (f) inserting or instructing the insertion of a cannula into the patient to create a single percutaneous entry point, wherein the cannula is inserted into the patient simultaneously with the preceding dilator; and/or (g) instructing the monitoring of an electrical circuit that includes a mapping contact on the preceding dilator to detect intrathecal penetration. The two medical devices can be two percutaneous leads for the delivery of electrical therapy to the patient.

From the foregoing, it will be appreciated that specific embodiments of the technology have been described herein for purposes of illustration, but that various modifications may be made without deviating from the various embodiments of the technology. For example, some of the embodiments described above include a stylet having a hub. In other embodiments, a stylet having no hub (and/or a removable hub) can be employed. Additionally, in some embodiments, a needle having a removable hub can be inserted into a patient to create a percutaneous entry point, and after the hub is removed, a dilator can be slid over the needle to expand the entry point. Furthermore, although the illustrated embodiments include dilators having round and elliptical shapes, dilators having a variety of other suitable shapes and sizes can be constructed in accordance with the present technology. For example, in some embodiments dilators can include oval shaped lumens. Furthermore, dilators in accordance with the present technology can have asymmetrical distal ends (e.g., scarfed or beveled ends) that can incrementally enter a percutaneous entry point as the dilator is inserted. That is, a portion of the distal end of the dilator can enter the percutaneous entry point before the remainder of the distal portion. Additionally, although the embodiments described above include several different combinations of various features or methods, embodiments in accordance with the present technology can include additional combinations of any of the features or methods. Accordingly, the disclosure and associated technology can encompass other embodiments not expressly shown or described herein.

What is claimed is:
1. A method for percutaneously implanting medical devices in a patient, the method comprising:

inserting or instructing insertion of a cannula into a patient, wherein the cannula includes a lumen;

inserting or instructing insertion of a preceding dilator into the patient via the lumen of the cannula;

removing or instructing removal of the cannula;

inserting or instructing insertion of a subsequent dilator into the patient via advancement of the subsequent dilator over the preceding dilator;

removing or instructing removal of the preceding dilator;

inserting or instructing insertion of a first medical device and a second medical device side by side into a final dilator; and advancing or instructing advancement of the first medical device and the second medical device into the patient.

2. The method of claim 1 wherein inserting or instructing insertion of the first medical device and the second medical device side by side into the final dilator includes inserting or instructing insertion of the first medical device and the second medical device side by side into a lumen of the final dilator, wherein the lumen of the final dilator includes an elliptical cross-sectional shape.

3. The method of claim 2 wherein the first medical and the second medical device comprise leads, each lead having a diameter, wherein the elliptical cross-sectional shape includes a major axis and a minor axis, wherein inserting or instructing insertion of the first medical device and the second medical device side by side into the lumen of the final dilator includes inserting or instructing insertion of the first medical device and the second medical device positioned side by side on the major axis.

4. The method of claim 1 wherein inserting or instructing insertion of the cannula into the patient includes inserting or instructing insertion of the cannula into the patient with a stylet positioned within the lumen of the cannula.

5. The method of claim 4, further comprising removing or instructing removal of the stylet prior to inserting or instructing insertion of the preceding dilator into the patient via the lumen of the cannula.

6. The method of claim 1 wherein the subsequent dilator comprises the final dilator.

7. The method of claim 1, further comprising inserting or instructing insertion of at least one additional dilator into the patient, prior to inserting or instructing insertion of the first medical device and the second medical device side by side into the final dilator.

8. The method of claim 1 wherein inserting or instructing insertion of a cannula into a patient includes aligning or instructing alignment of a stylet tip with a tip of the cannula to produce a percutaneous entry point in the patient without coring a hole in the patient.

9. The method of claim 8 wherein aligning or instructing alignment of the stylet tip with the tip of the cannula includes mating or instructing mating of a hub on the stylet with a hub on the cannula.

10. The method of claim 1 wherein the first medical device and the second medical device comprise spinal cord stimulation leads having electrical contacts, and wherein the method further comprises positioning or instructing positioning of the spinal cord stimulation leads to deliver electrical signals via the contacts to a spinal cord region of the patient.

* * * * *